(12) United States Patent
Dellea et al.

(10) Patent No.: US 11,358,091 B2
(45) Date of Patent: Jun. 14, 2022

(54) GAS TREATMENT SYSTEM HAVING INCREASED SERVICE LIFE

(71) Applicant: COMMISSARIAT A L'ENERGIE ATOMIQUE ET AUX ENERGIES ALTERNATIVES, Paris (FR)

(72) Inventors: Olivier Dellea, Grenoble (FR); Arthur Roussey, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 17/280,431

(22) PCT Filed: Sep. 25, 2019

(86) PCT No.: PCT/FR2019/052258
§ 371 (c)(1),
(2) Date: Mar. 26, 2021

(87) PCT Pub. No.: WO2020/065215
PCT Pub. Date: Apr. 2, 2020

(65) Prior Publication Data
US 2022/0001323 A1 Jan. 6, 2022

(30) Foreign Application Priority Data
Sep. 28, 2018 (FR) ..................... 1859034

(51) Int. Cl.
*B01D 53/04* (2006.01)
*B01D 53/56* (2006.01)
(Continued)

(52) U.S. Cl.
CPC ....... *B01D 53/0446* (2013.01); *B01D 53/565* (2013.01); *B01D 53/75* (2013.01);
(Continued)

(58) Field of Classification Search
CPC ........ B01D 2257/106; B01D 2257/708; B01D 2259/402; B01D 2259/40083;
(Continued)

(56) References Cited

U.S. PATENT DOCUMENTS 4,167,484 A * 9/1979 Morikawa ............... C01B 13/11
250/436
6,358,374 B1 3/2002 Obee et al.
(Continued)

FOREIGN PATENT DOCUMENTS

| CN | 107469562 A | 12/2017 |
| EP | 0 431 648 A1 | 6/1991 |
| FR | 2 972 932 A1 | 9/2012 |

OTHER PUBLICATIONS

International Search Report dated Jan. 29, 2020 in PCT/FR2019/052258 filed Sep. 25, 2019, 2 pages.
(Continued)

*Primary Examiner* — Timothy C Vanoy
(74) *Attorney, Agent, or Firm* — Oblon, McClelland, Maier & Neustadt, L.L.P.

(57) ABSTRACT

In order to limit exposure of a fan (50) and of eventually other internal components to oxidizing species induced by the operation of an ozone generator (70), a gas treatment system (10) of the type operating alternately in treatment mode and in regeneration mode comprises two adsorption devices (60, 80) which are arranged respectively upstream and downstream of the ozone generator.

12 Claims, 6 Drawing Sheets

(51) Int. Cl.
*B01D 53/75* (2006.01)
*B01D 53/82* (2006.01)
*B01D 53/86* (2006.01)
*C01B 13/10* (2006.01)

(52) U.S. Cl.
CPC ......... *B01D 53/82* (2013.01); *B01D 53/8675* (2013.01); *C01B 13/10* (2013.01); *B01D 2257/106* (2013.01); *B01D 2257/404* (2013.01); *B01D 2257/708* (2013.01); *B01D 2259/402* (2013.01); *B01D 2259/40083* (2013.01); *B01D 2259/4508* (2013.01)

(58) Field of Classification Search
CPC ...... B01D 2251/104; B01D 2259/4508; B01D 2258/06; A61L 2/202; A61L 9/00; A61L 9/014; A61L 9/015; C01B 13/10; B01J 19/24; B01J 19/248; B01J 2219/00247; B01J 2219/02; B01J 2219/2401
See application file for complete search history.

(56) References Cited

U.S. PATENT DOCUMENTS

2004/0140194 A1 7/2004 Taylor, Jr. et al.
2008/0210084 A1 9/2008 Ota et al.

OTHER PUBLICATIONS

Preliminary French Search Report dated Jul. 16, 2019 in French Patent Application No. 1859034 filed Sep. 28, 2018, 2 pages (with Translation of Category).

* cited by examiner

GAS TREATMENT SYSTEM HAVING INCREASED SERVICE LIFE

TECHNICAL FIELD

The present invention concerns a gas treatment system, such as a system for purifying the air inside buildings, capable of operating alternately in a treatment mode and in a regeneration mode, comprising:

an inlet and an outlet, and a main path connecting the inlet to the outlet and comprising a treatment portion so as to enable the circulation of a main gas stream from the inlet to the outlet, passing via the treatment portion, in the treatment mode;

at least one secondary path having two opposite ends connected to the main path, respectively upstream and downstream of the treatment portion, so that the secondary path and at least the treatment portion of the main path form a recirculation loop enabling closed-loop circulation of a recirculation gas stream in the treatment portion of the main path, in the regeneration mode;

a fan disposed in the recirculation loop and configured at least to propel the recirculation gas stream within the recirculation loop in a predetermined circulation direction, in the regeneration mode;

a first adsorption device disposed in the treatment portion of the main path, downstream of the fan with respect to the predetermined circulation direction, and capable of adsorbing predefined substances potentially present in the main gas stream, such as volatile organic compounds, in the treatment mode;

an ozone generator disposed in the treatment portion of the main path, downstream of the fan with respect to the predetermined circulation direction, and capable of generating ozone in the regeneration mode; and a switching device configured to keep the inlet and the outlet open, prevent the circulation of the main gas stream via the secondary path or each secondary path, and keep the ozone generator stopped, in the treatment mode, and to keep the inlet and the outlet closed, allow the circulation of the recirculation gas stream in the secondary path or in each secondary path, and keep the ozone generator in operation, in the regeneration mode.

The invention also concerns a gas treatment method, in particular a method for purifying the air inside buildings, by means of such a system.

PRIOR ART

Various gas treatment technologies are known, in particular with regard to the treatment of the air inside buildings. These aim, in particular, to reduce the concentrations of volatile organic compounds (VOCs).

In the foregoing and in what follows, a "volatile organic compound" is defined in accordance with European Council Directive 1999/13/EC of the 11 Mar. 1999, by virtue of which:

a volatile organic compound is "any organic compound having at 293.15 K (i.e. 20° C.) a vapour pressure of 0.01 kPa (i.e. $9.87.10^5$ atm) or more, or having a corresponding volatility under the particular conditions of use" (cf. paragraph 17 of Article 2 of the Directive);

an organic compound is "any compound containing at least the element carbon and one or more of hydrogen, halogens, oxygen, sulphur, phosphorus, silicon or nitrogen, with the exception of carbon oxides and inorganic carbonates and bicarbonates" (cf. paragraph 16 of Article 2 of the Directive).

Hence, the following are considered to be volatile organic compounds: certain saturated or unsaturated acyclic hydrocarbons, such as ethane, propane, n-butane, n-hexane, ethylene, propylene, 1,3-butadiene and acetylene, certain saturated or unsaturated non-aromatic, cyclic hydrocarbons, such as cyclopropane, cyclopentane and cyclohexane, certain aromatic hydrocarbons such as benzene, toluene, the xylenes and ethylbenzene, certain halogenated hydrocarbons such as dichloromethane, trichloromethane, chloroethane, trichloroethylene and tetrachloroethylene, certain alcohols such as methanol, ethanol, 1-propanol, 2-propanol, ethylene glycol and propylene glycol, certain aldehydes such as formaldehyde, acetaldehyde, propanal and 2-propenal (or acrolein), certain ketones such as acetone, methyl ethyl ketone, 2-butanone and methyl vinyl ketone, certain esters such as methyl acetate, ethyl acetate, isopropyl acetate and isoamyl butyrate, certain ethers such as diethyl ether, ethylene glycol n-butyl ether (EGBE) and 1,4-dioxane, certain acids such as acetic acid and propanoic acid, certain amines such as ethylamine, dimethylamine, trimethylamine, diethylamine and amylamine, certain amides such as dimethylformamide, sulphur compounds such as methyl mercaptan (or methanethiol) and ethyl mercaptan (or ethanethiol), and certain nitriles such as acetonitrile and acrylonitrile.

Gas treatment technologies, in particular technologies for treating air inside buildings, are based on physical phenomena such as:

physical adsorption: the principle of adsorption is based on the property possessed by solids (adsorbants) of fixing certain gases (adsorbates) on their surface. Pollutants are generally adsorbed on activated carbons or zeolites (these two materials have the advantage of having a large specific surface area and thus a large storage capacity). This is an efficient, low-cost technology but has the disadvantage of needing the filters to be changed very regularly in order that they do not become saturated and to avoid the re-emission of the pollutants.

Chemical adsorption or chemisorption: the process results from a chemical reaction with the forming of covalent or ionic bonds between the adsorbate molecule and the adsorbant surface. The process therefore requires that the filters are regularly replaced.

Ozonation: this method consists in passing the polluted air through a medium with a high ozone concentration (generated by UV lamp or cold plasma). This is therefore a method for direct oxidation of pollutants by ozone and its radicals in the gaseous volume. It is known that this method can generate pollutant products.

Photolysis: the polluted air is passed through a high-energy UV beam. It is admitted that the process can also generate pollutant products. Furthermore, UV light constitutes a potential danger for the user, and this method requires a large amount of energy.

Photocatalysis: UV radiation is combined with a photocatalyst (generally titanium dioxide) in order to generate radicals capable of degrading pollutants such as VOCs to obtain H2O or CO2, and capable of killing pathogenic species. The disadvantages are the possibility of re-emitting products connected to the degradation processes, low efficiency and a low conversion rate.

Catalytic oxidation: catalytic materials are used to degrade pollutants such as VOCs. In order to be efficient however, this method requires high temperatures (greater than 300° C.) and long residence times, which result in a high energy consumption.

Hence, these gas treatment techniques can be classified in three categories:

so-called recuperative methods, in which the gas stream passes through adsorbent or absorbent materials. The principle is to capture the pollutants on a substrate and to periodically renew this substrate after clogging.

so-called destructive methods, consisting of continuously destroying the pollutants present in the gas stream, for example by thermal or catalytic oxidation, by biological treatments, by photocatalysis or by absorption with chemical reaction.

hybrid processes, both recuperative and destructive, which are separated into two steps. A first step consists in capturing the pollutants on a substrate, while a second step consists in destroying them while regenerating the substrate. During the second step, the destruction takes place through the controlled emission of oxidant species such as ozone, atomic oxygen or hydroxyl radicals, these species being highly reactive and not very selective with regard to the nature of the chemical species to be destroyed.

In the recuperative and destructive methods, the second step (the step of destroying pollutants) is based in general on the use of a non-thermal plasma source at atmospheric pressure.

A non-thermal plasma (also called cold plasma) is based on the selected acceleration of electrons so that they attain a temperature of 10,000 to 250,000 K, although the temperature of the gas remains substantially unchanged. The collision of the electrons with the $O_2$, $N_2$ and $H_2O$ molecules present in the gas leads to the production of excited molecules ($N_2^*$, $O_2^*$, $O_3^*$, $OH^*$, etc.). These excited molecules emit photons or heat in order to lose this energy. This energy forms reactive species and unstable radicals ($OH^*$ and $O^*$) which contribute to the oxidation reactions and thus have the ability to break down the pollutants into less hazardous species such as $CO_2$, $H_2O$, HX and $X_2$ (X being a halogen).

At the outlet of plasma reactors of this type, the most commonly observed stable species comprise ozone and nitrogen oxides, such as NO, $NO_2$, $N_2O$ and $HNO_3$.

Analogous observations can be made in the case of other types of ozone generator, such as ultraviolet radiation sources.

Furthermore, it is known to combine ozone generators with catalysts and/or with a heat source, in order to obtain further oxidation of pollutants.

Documents WO2004/014439 and FR2972932 disclose systems having the features given in the introduction and implementing hybrid methods by means of a non-thermal plasma source as explained above.

The inventors have, however, noticed that these systems have certain disadvantages, in particular a short service life and a risk of releasing nitrogen oxides into the surrounding air.

DISCLOSURE OF THE INVENTION

The invention aims, in particular, to at least partially avoid the above stated disadvantages.

To this effect, the system proposed by the invention further comprises a second adsorption device suitable for adsorbing the predefined substances, disposed in the treatment portion of the main path, downstream of the fan with respect to the predetermined circulation direction, and such that the first and second adsorption devices are respectively disposed upstream and downstream of the ozone generator with respect to the predetermined direction of circulation.

The inventors have analysed that the short service life of known types of gas treatment systems was at least partially attributable to the phenomena of corrosion of metal parts, in particular the fan or fans, and to the ageing of certain polymers used in the construction of such systems, on contact with oxidising species including ozone and other species that can be produced by the ozone generator.

The arrangement of the ozone generator between two adsorption devices within the treatment portion, as proposed by the invention in its most general aspect, makes it possible to limit the exposure of the fan to oxidising species induced by the operation of the ozone generator.

In preferred embodiments of the invention, the system can have one or more of the following characteristics, taken alone or according to all the technically possible combinations:

the secondary path comprises an active portion configured to modify the composition of the recirculation gas stream, in the regeneration mode;

the active portion comprises a treatment assembly comprising a catalysis device capable of catalysing at least one reaction among the oxidation reactions of the predefined substances, and wherein the fan, the first adsorption device, the ozone generator, the second adsorption device and the treatment assembly are arranged in that order with respect to the predetermined direction of circulation;

the treatment assembly further comprises an ozone treatment device suitable for trapping or breaking down ozone, and arranged downstream of the catalyst device with respect to the predetermined direction of circulation;

the treatment assembly further comprises a trapping device suitable for trapping at least one product of at least one reaction among the oxidation reactions of the predefined substances, and arranged downstream of the ozone treatment device with respect to the predetermined direction of circulation;

the active portion comprises a nitrogen oxides treatment device, suitable for trapping nitrogen oxides (NOx);

the nitrogen oxides treatment device is arranged between the second adsorption device and the treatment assembly;

the secondary path is a first secondary path, the active portion is a first active portion, and the recirculation loop is a first recirculation loop, the system further comprising a second secondary path not comprising the first active portion and having two opposite ends connected to the main path, respectively upstream and downstream of the treatment portion, so that the second secondary path and at least the treatment portion of the main path form a second recirculation loop allowing a closed-loop circulation of the recirculation gas stream in the treatment portion of the main path, in the regeneration mode, the second secondary path comprising a second active portion not included in the first secondary path and comprising at least one particle filter, the switching device being configured to cause recirculation phases to follow one another, wherein the recirculation gas stream circulates respectively in the first recirculation loop and in the second recirculation loop, in the regeneration mode;

the system comprises a third secondary path not comprising the respective active portions of the first secondary path and of the second secondary path and having two opposite ends connected to the main path, respectively upstream and downstream of the treatment portion, so that the third secondary path and at least the treatment portion of the main path form a third recirculation loop allowing a closed-loop circulation of the recirculation gas stream in the treatment portion of the main path, in the regeneration mode, the third secondary path comprising a third active portion not included in the first secondary path or in the second secondary path and configured to modify the composition of the recirculation gas stream, in the regeneration mode, the switching device being configured to cause recirculation phases to follow one another, wherein the recirculation gas stream circulates respectively in the first recirculation loop, in the third recirculation loop and in the second recirculation loop, in the regeneration mode;

the third active portion comprises a nitrogen oxides treatment device, suitable for trapping nitrogen oxides (NOx);

the fan is housed in the treatment portion of the main path and is configured to propel the main gas stream within the main path from the inlet to the outlet, in the treatment mode.

The invention also concerns a method for gas treatment by means of a system of the above-described type, alternately comprising:

using the system in the treatment mode, in which the switching device keeps the inlet and the outlet open, prevents the circulation of the main gas stream via the secondary path and keeps the ozone generator stopped, whereby the main gas stream is admitted by the inlet, then passes into the first and second adsorption devices, wherein all or part of the predefined substances potentially present in the main gas stream are retained by adsorption, then the main gas stream, depleted of any predefined substances, is discharged via the outlet; and using the system in regeneration mode, in which the switching device keeps the inlet and the outlet closed, allows the circulation of the recirculation gas stream in the secondary path, and keeps the ozone generator operating, whereby:

a) the recirculation gas stream, driven by the fan in the recirculation loop, charges with ozone produced by the ozone generator and carries away the ozone, and any active species induced by the ozone, into the second adsorption device, wherein any predefined substances previously adsorbed by the second adsorption device are oxidised and are desorbed on contact with the ozone and any other active species induced by the ozone, b) the first adsorption device receives the ozone, and any active species induced by the ozone, potentially backscattering into the recirculation gas stream, whereby any predefined substances previously adsorbed by the first adsorption device are oxidised and are desorbed on contact with the ozone and any other active species induced by the ozone.

BRIEF DESCRIPTION OF THE FIGURES

The invention will be better understood and other details, features and advantages thereof will appear on reading the following description, provided by way of a non-limiting example and with reference to the attached drawings, in which.

DETAILED DISCLOSURE OF PREFERRED EMBODIMENTS

Figure 1:
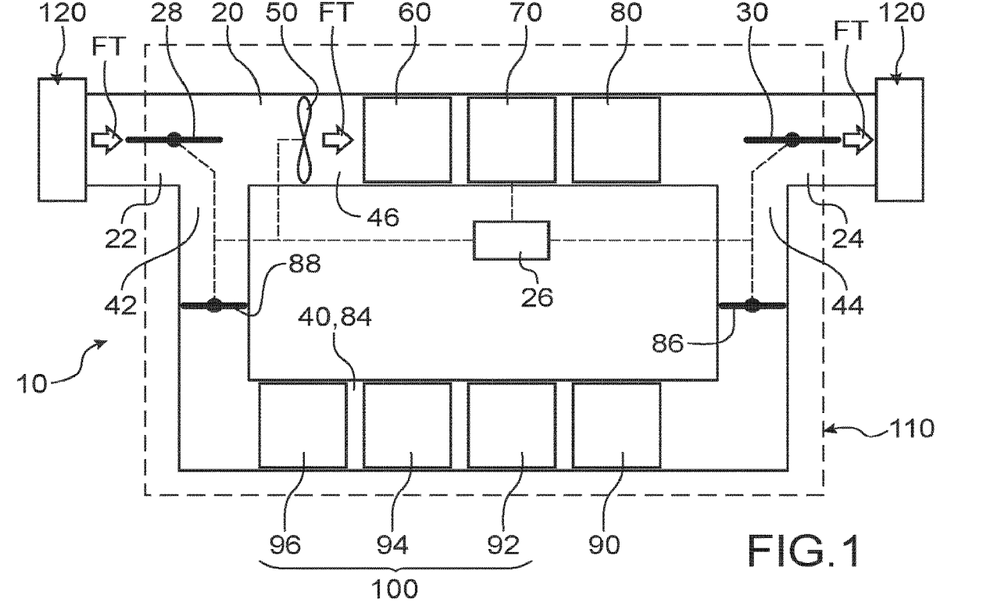
FIG. 1 is a process diagram of a gas treatment system according to a first preferred embodiment of the invention, illustrated operating in the treatment mode.
Figure 2:
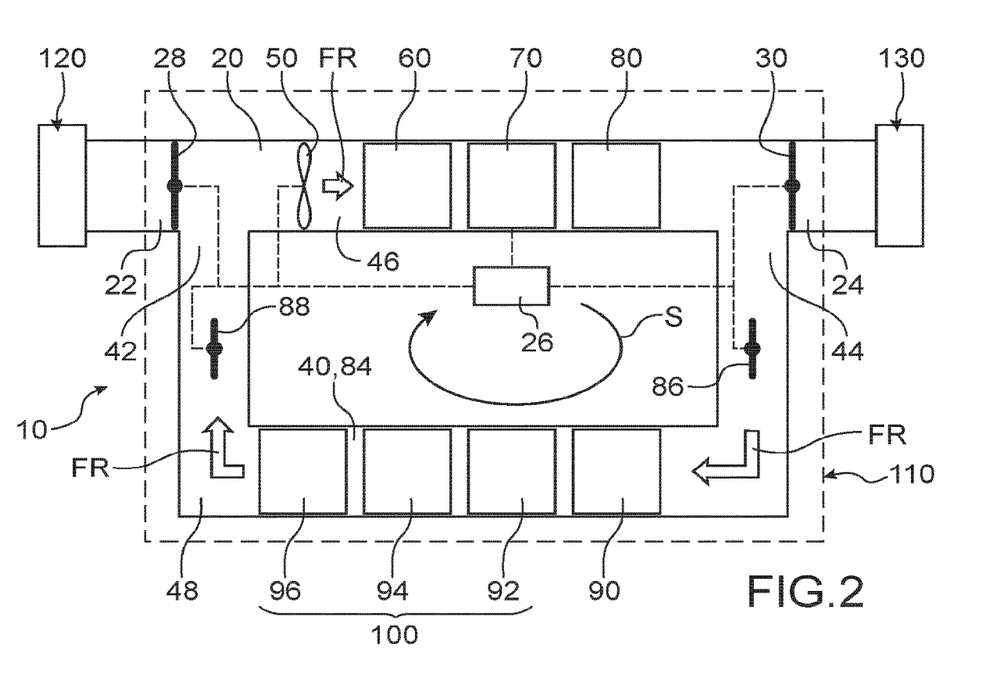
FIG. 2 is a view similar to FIG. 1, illustrating the system operating in regeneration mode.

FIGS. 1 and 2 schematically illustrate a gas treatment system 10 according to a preferred embodiment of the invention, in this case a system intended for purification of the air inside buildings.

The system 10 is intended to operate alternately in a treatment mode, illustrated in FIG. 1 and in a regeneration mode, illustrated in FIG. 2, as will appear more clearly in the following.

The system 10 comprises a main path 20 connecting an inlet 22 of the system to an outlet 24 of the system. In the treatment mode, the system 10 is configured to allow circulation of a gas stream FT in the main path 20 from the inlet 22 to the outlet 24, and to remove from the gas stream FT one or more predefined substances such as pollutants, in particular volatile organic compounds, within the main path 20.

In the foregoing and in what follows, a "path" is, in general, a gas flow path defined within a channel or a set of channels connected end-to-end, a given channel being able to participate in the forming of a plurality of paths.

The system 10 further comprises a switching device capable of switching the system from treatment mode to regeneration mode, and vice versa. The switching device is, for example, configured to operate the mode switching automatically and regularly, for example so as to keep the system 10 in treatment mode for 23 hours per day and in regeneration mode for 1 hour per day.

The switching device comprises an inlet valve 28 arranged in the inlet 22, and an outlet valve 30 arranged in the outlet 24. Here, "valve" shall mean any device capable of interrupting and re-establishing, on command, the circulation of a gas stream, by respectively adopting a closed configuration and an open configuration. Such a device is sometimes termed an "air damper".

The switching device further comprises a control unit 26 for controlling the inlet valve 28 and outlet valve 30, so that these keep the inlet 22 and the outlet 24 open in treatment mode (FIG. 1) and keep the inlet 22 and the outlet 24 closed (in a sealed manner) in regeneration mode (FIG. 2).

The system 10 further comprises a secondary path 40 separated from the main path 20 and having two opposite ends 42, 44 connected to the main path 20 in two zones spaced apart from one another and situated respectively upstream and downstream from a treatment portion 42 defined within the main path 20. Thus, the secondary path 40 and the treatment portion 46 (or a larger portion of the main path, including the treatment portion 46) form a recirculation loop 48, in regeneration mode, in other words when the inlet 22 and the outlet 24 are kept closed by the switching device (FIG. 2). This mode of operation also allows the closed-loop circulation of a recirculation gas stream FR in the recirculation loop 48, and therefore in particular in the treatment portion 46.

The switching device further comprises an anti-bypass device controlled by the control unit 26 between a closed configuration, in which the anti-bypass device obstructs (in a sealed manner) the secondary path 40 and prevents the main gas stream FT from bypassing the treatment portion 46 by passing via the secondary path 40 in treatment mode, and an open configuration, in which the anti-bypass device allows the circulation of the recirculation gas stream FR in the secondary path 40, in regeneration mode, as will appear more clearly in the following.

The system 10 further comprises a fan 50, for example an axial fan, disposed in the recirculation loop 48 and configured to propel the recirculation gas stream FR within the recirculation loop 48 in a predetermined circulation direction S, in the regeneration mode (FIG. 2).

In the illustrated example, the fan 50 is housed in the treatment portion 46 of the main path 20 and is configured to propel the main gas stream FT within the main path from the inlet 22 to the outlet 24, in the treatment mode.

The same fan 50 thus enables the propulsion of the air in both operating modes of the system.

Of course, the system can nevertheless be provided with one or more additional fans, for example in the secondary path 40.

The system 10 further comprises a first adsorption device 60 and a second adsorption device 80 disposed in the treatment portion 46 of the main path 20, downstream of the fan 50 with respect to the predetermined circulation direction S (FIG. 2), and capable of adsorbing predefined substances, for example volatile organic compounds (VOCs), in the treatment mode (FIG. 1).

The adsorption devices 60 and 80 can be of any type known in the prior art. These devices are preferably each in the form of a honeycomb structure, made for example of titanium dioxide, zirconium dioxide or magnesium oxide, provided with an adsorbent coating. This coating consists, for example, of silica, zeolite, an Al/Si mixture, and other possible elements such as nanoparticles of one or more metals chosen among gold, silver, copper, platinum, manganese, palladium and the combination of such metals. The adsorbent coating preferably has a thickness between 10 and 200 microns, more preferably between 20 and 150 microns, and a pore size between 3 and 20 nanometres.

The system 10 further comprises an ozone generator 70 disposed in the treatment portion 46 of the main path 20, and suitable for generating ozone in the regeneration mode. More precisely, the ozone generator 70 is arranged so that the first and second adsorption devices 60, 80 are disposed respectively upstream and downstream of the ozone generator 70 with respect to the predetermined circulation direction S (FIG. 2).

The ozone generator 70 is controlled by the control unit 26, which is configured to keep the ozone generator 70 stopped in the treatment mode, and to keep it operating in the regeneration mode.

The ozone generator 70 is preferably capable of generating 0.5 to 50 grammes of ozone per hour.

The ozone generator 70 is preferably a non-thermal plasma reactor, of the surface discharge (SD) type, for example.

Alternatively, the ozone generator 70 may be a non-thermal plasma reactor of another type, or even a source of ultraviolet (UV) radiation.

In another alternative, the ozone generator 70 may comprise a plurality of ozone generation devices of different types, for example a non-thermal plasma reactor and an ultraviolet (UV) radiation source.

In preferred embodiments of the invention, the secondary path 40 comprises an active portion 84 configured to modify the composition of the recirculation gas stream FR, in the regeneration mode, as will appear more clearly in the following.

In this case, the anti-bypass device comprises a first isolation valve 86 arranged upstream of the active portion 84 in the secondary path 40 or in the inlet thereof, and a second isolation valve 88 arranged downstream of the active portion 84 in the secondary path 40 or at the outlet thereof. These isolation valves 86 and 88 are controlled by the control unit 26 so that the isolation valves 86, 88 adopt a closed configuration and thus isolate (in a sealed manner) the active portion 84 of the secondary path 40 of the main path 20 in the treatment mode, and so that the isolation valves 86, 88 adopt an open configuration and thus set the active portion 84 of the secondary path 40 in communication with the main path 20, in the regeneration mode. This configuration of the anti-bypass device makes it possible to completely isolate the active portion 84 of the main path 40, in the treatment mode, and thus prevent the active portion 84 from acting on the main gas stream FT.

More precisely, the active portion 84 preferably comprises the following devices, arranged in this order with respect to the circulation direction S:

a nitrogen oxides treatment device 90 suitable for reducing the concentration of nitrogen oxides (NOx) in the recirculation gas stream FR, such compounds possibly being generated, in particular, by the ozone generator;

a catalysis device 92 capable of catalysing at least one reaction among the oxidation reactions of the predefined substances;

an ozone treatment device 94 suitable for reducing the concentration of ozone in the recirculation gas stream FR; and a trapping device 96 suitable for trapping at least one product of at least one reaction among the oxidation reactions of the predefined substances, capable of resulting from oxidation reactions in the at least one among the catalysis device 92 and the first and second adsorption devices 60 and 80. This trapping device 96 is useful in that it concerns products for which the kinetic break down reactions would be too slow to allow their breaking down during an operating cycle in regeneration mode.

The nitrogen oxides treatment device 90 is preferably a cartridge formed of a porous casing containing a nitrogen oxide trapping material present in dispersed form, for example in the form of grains, beads, batons or fibres, or in honeycomb form.

The nitrogen oxide trapping material is preferably a material comprising one or more metal oxides such as transition metal oxides, alkaline earth metal oxides (for example barium or magnesium oxide), or rare earth oxides (for example cerium oxide), or carbonates of formula $M(CO3)x$ where M is chosen among the alkaline earths and lanthanides, or even zeolites, the latter preferably having a pore size between 3 and 20 nanometres.

This material is preferably in the form of grains of diameter between 1 and 3 millimetres.

The catalysis device 92 is preferably a cartridge formed of a porous casing containing a catalysis material present in dispersed form, for example in the form of grains, particles or fibres, or in honeycomb form.

The catalysis material is preferably a low-temperature (for example between 20 and 100 degrees Celsius) oxidation reaction catalyst, composed of metal particles chosen among gold, silver, copper, manganese, platinum and palladium, or a mixture of such particles, dispersed on an oxide such as alumina, silica, titanium dioxide, zirconium dioxide and magnesium oxide, or a mixture of such oxides.

This material is preferably in the form of grains of diameter between 1 and 3 millimetres.

The ozone treatment device 94 is preferably a cartridge formed of a porous casing containing an ozone treatment material present in dispersed form, for example in the form of grains, particles or fibres, or in honeycomb form.

"Ozone treatment" shall be understood to mean either ozone trapping or the catalysis of an ozone conversion reaction into other compounds (considered to be non-harmful or less harmful).

The ozone treatment material is preferably a material capable of breaking down ozone, such as a mixture of $MnO_x$ and $CuO_y$ (x and y being integers), optionally dispersed on oxides such as alumina or silica, or on a zeolite, so as to present a specific surface area of between 10 and 1000 m2/g, preferably between 150 and 600 m2/g.

This material is preferably in the form of grains of diameter between 1 and 3 millimetres.

Finally, the trapping device 96 is preferably a cartridge formed of a porous casing containing a trapping material present in dispersed form, for example in the form of grains, particles or fibres, or in honeycomb form.

The trapping material is preferably activated carbon.

In the terminology of the invention, the catalysis 92, ozone treatment 94 and trapping 96 devices constitute a treatment assembly 100, arranged downstream of the nitrogen oxide treatment device 90 with respect to the circulation direction S.

The arrangement of the nitrogen oxides treatment device 90 upstream of the treatment assembly 100 is particularly advantageous due to the fact that nitrogen oxides 90 are likely to interfere with the operation of the treatment assembly 100. Hence, the reduction in NOx concentration upstream of the catalysis 92 and ozone treatment 94 devices avoids reactions involving NOx coming into competition with reactions involving the predefined substances, in this case VOCs, and ozone, at these two devices.

Analogously, the arrangement of the ozone treatment device 94 upstream of the trapping device 96 is particularly advantageous due to the fact that ozone may be capable of degrading the trapping device 96, in particular when the latter comprises activated carbon as in the illustrated example. Thus, the reduction in the concentration of ozone upstream of the trapping device 96 makes it possible to avoid ozone degrading the trapping device 96.

Furthermore, the control unit 26 is preferably configured to control the fan 50, so that the fan 50 turns at a lower speed in the regeneration mode than in the treatment mode. A lower speed of the gas stream makes it possible to promote the phenomena of adsorption, desorption and, if applicable, trapping and catalysis.

The above-described elements of the system 10 form a main unit 110, to which can optionally be added an additional inlet module 120 arranged in the inlet 22 and comprising for example a particle filter, and/or an additional outlet module 130 arranged in the outlet 24 and comprising for example an ion generator, and/or one or more additional filters or adsorbent devices, and/or another particle filter.

In operation, the system 10 can implement a gas treatment method, for example a method for purifying the air in buildings, wherein the treatment mode and the regeneration mode are implemented alternately.

In the treatment mode, the fan 50 propels the main gas stream FT from the inlet 22 to the outlet 24, which are kept open, the ozone generator 70 being stopped, and the active portion 84 of the secondary path 40 being isolated from the main path 20 by the isolation valves 86 and 88 (FIG. 1), or, more generally, the circulation of the main gas stream FT via the secondary path 40 being prevented by the anti-bypass device in closed configuration.

The predefined substances, for example VOCs, potentially present in the main gas stream FT, are adsorbed by the adsorption devices 60 and 80, so that the gas, in this case air, discharged via the outlet 24, is purified or at least depleted of these substances.

Regularly, in order to avoid saturation of the adsorption devices 60 and 80, the system 10 switches into regeneration mode, by closing of the inlet 22 and of the outlet 24 by the inlet valves 28 and outlet valves 30 respectively, switching of the anti-bypass device into open configuration, in this case opening isolation valves 86 and 88, allowing the active portion 84 of the secondary path 40 to be placed in communication with the main path 20, and the starting of the ozone generator 70, by the switching device 26. Where appropriate, the heat source is brought into operation.

In this operating mode, the fan 50 forces the circulation of the recirculation gas stream FR in the recirculation loop 48. For this purpose, the operating power of the fan 50 is preferably reduced with respect to its power in the treatment mode.

A part, in principle the majority, of the ozone generated by the ozone generator 70, is transported to the second adsorption device 80 by the recirculation gas stream FR, while another part, in principle a minority, of the ozone generated by the ozone generator 70, moves towards the first adsorption device 60 by backscattering.

Oxidation reactions of the predefined substances, preferably adsorbed by the adsorption devices 60 and 80, are produced within these two devices, due to the presence, within these devices, of ozone and/or potentially other active species induced by the operation of the ozone generator 70, as explained above. This results in a gradual regeneration of the adsorption devices 60 and 80, with the release of the adsorption sites, by desorption of the predefined substances and/or compounds resulting from the oxidation of these predefined substances on the adsorption sites.

The arrangement of the first adsorption device 60 between the fan 50 and the ozone generator 70 makes it possible, in particular, to limit the exposure of the fan 50 to ozone, and to other potential oxidising species, backscattering upstream with respect to the circulation direction S, from the ozone generator 70.

The recirculation gas stream FR then passes into the nitrogen oxides treatment device 90, which makes it possible to reduce the concentration of nitrogen oxides in this recirculation gas stream FR.

The recirculation gas stream FR, depleted of nitrogen oxides, or devoid thereof, then passes into the treatment assembly 100.

The recirculation gas stream FR first encounters the catalysis device 92, which maximises the oxidation of the predefined substances by ozone and/or by any other oxidising species induced by the operation of the ozone generator 70.

Then, the recirculation gas stream FR encounters the ozone treatment device 94, which makes it possible to drastically reduce the concentration of ozone in the recirculation gas stream, by breaking down (or, alternatively, trapping) the ozone.

Finally, the recirculation gas stream FR encounters the trapping device 96 which makes it possible to trap any oxidation products previously generated in at least one among the catalysis device 92 and the first and second adsorption devices 60 and 80. The oxidation products considered therefore, in general, originate from oxidation reactions of the predefined substances.

After having travelled through the entire recirculation loop 48, the recirculation gas stream FR again encounters the fan 50 and continues its closed-loop circulation as described above.

The arrangement of the ozone treatment device 94 in the secondary path 40 limits the exposure of the fan 50 to the fraction of the ozone carried away by the recirculation gas stream FR from the ozone generator 70 and remaining in this recirculation gas stream at the outlet of the second adsorption device 80.

The inventors have analysed that the short service life of known types of gas treatment systems was at least in part due to corrosion phenomena of metal parts and oxidation of parts made from polymer, in particular the fan or fans, by oxidising species, primarily ozone, but also nitrogen oxides.

The arrangement of the first adsorption device 60 between the fan 50 and the ozone generator 70 within the main path 20, upstream of the ozone generator with respect to the circulation direction S, on the one hand, and the arrangement of the ozone treatment device 94 in the secondary path 40, downstream of the ozone generator with respect to the circulation direction 5, on the other hand, limits the exposure of the fan 50 to ozone and to the other potential oxidising substances, and thus increases the service life thereof.

In addition, these features limit the concentration of ozone in a major part of the recirculation loop 48, and thus limit the exposure to ozone of any other parts of the system made from metal or polymer.

Furthermore, the presence of the nitrogen oxides treatment device 90 within the recirculation loop 48, downstream of the ozone generator 70, limits the exposure of the fan 50 (and any other metal or polymer parts) to nitrogen oxides, and therefore here too increases the service life of the fan 50 (and any other metal parts).

The nitrogen oxides treatment device 90 also minimises the risk that the gas discharged by the outlet 24, in the treatment mode, contains nitrogen oxides generated during an earlier operating phase in regeneration mode.

Analogous advantages arise from the presence, in the active portion 84 of the secondary path 40, of the trapping device 96, since certain oxidation products, which may remain present at the outlet of the ozone treatment device 94, may have a corrosive and/or harmful nature if they were to be discharged by the system.

The system 10 described above involves a treatment, in a same recirculation loop, of all of the predefined substances and of any other species to be treated that are induced by the operation of the ozone generator 70.

In certain cases, it may be advantageous to successively treat different substances or species by means of a plurality of recirculation loops, each recirculation loop being able to be configured for a generic treatment, in other words targeting all the predefined substances and any other species to be treated, or for a specific treatment of one or more of the predefined substances and any other species to be treated. Recirculation loops dedicated to specific treatments have, in particular, the advantage of a reduced pressure drop compared to a recirculation loop that comprises all the treatments.

To this effect, FIGS. 3 to 7 illustrate gas treatment systems according to other preferred embodiments of the invention, which are distinguished from the system 10 described above due to the fact that these systems comprise a plurality of secondary paths.

In these systems, for reasons of clarity, the secondary path 40, the active portion 84 and the recirculation loop 48, are respectively denoted first secondary path, first active portion and first recirculation loop.

Figure 3:
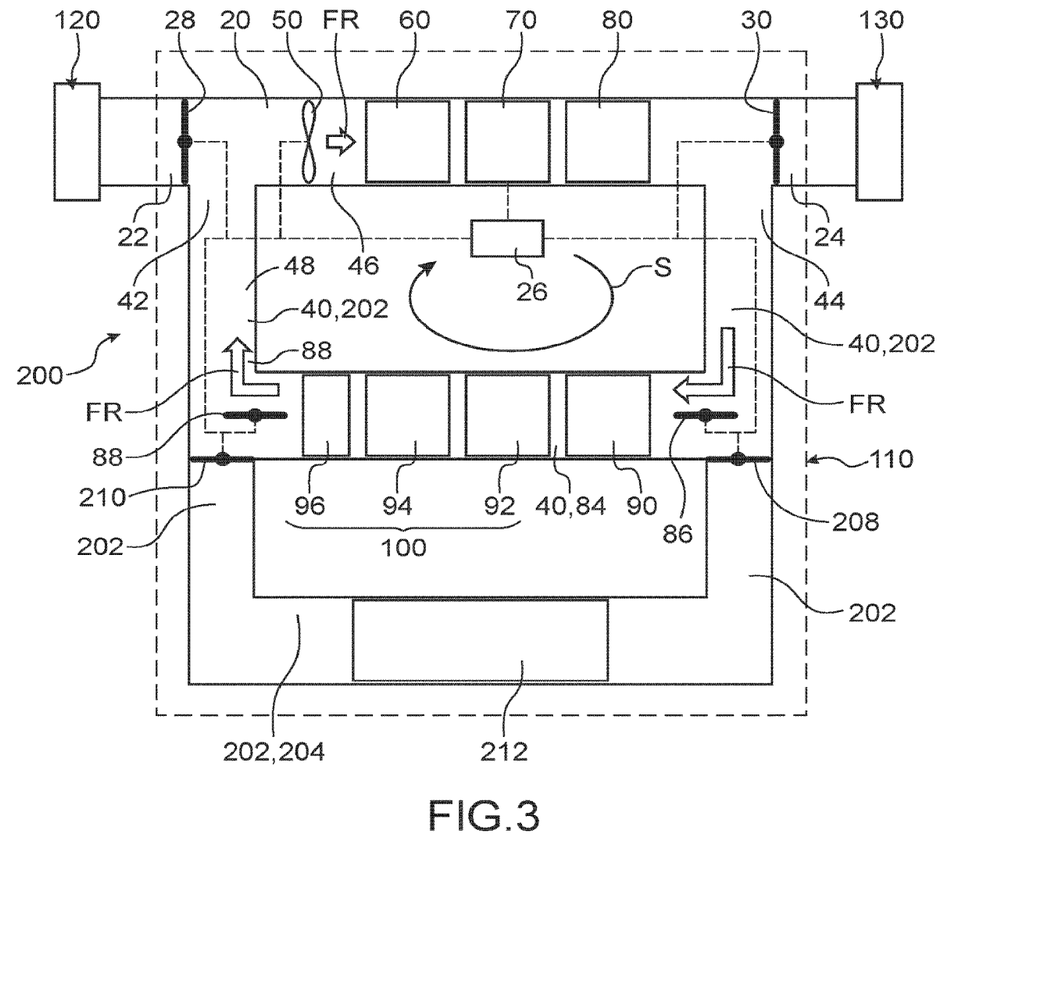
FIGS. 3 and 4 are views similar to FIG. 1, illustrating a gas treatment system according to a second preferred embodiment of the invention, operating respectively in two phases of its regeneration mode.
Figure 4:
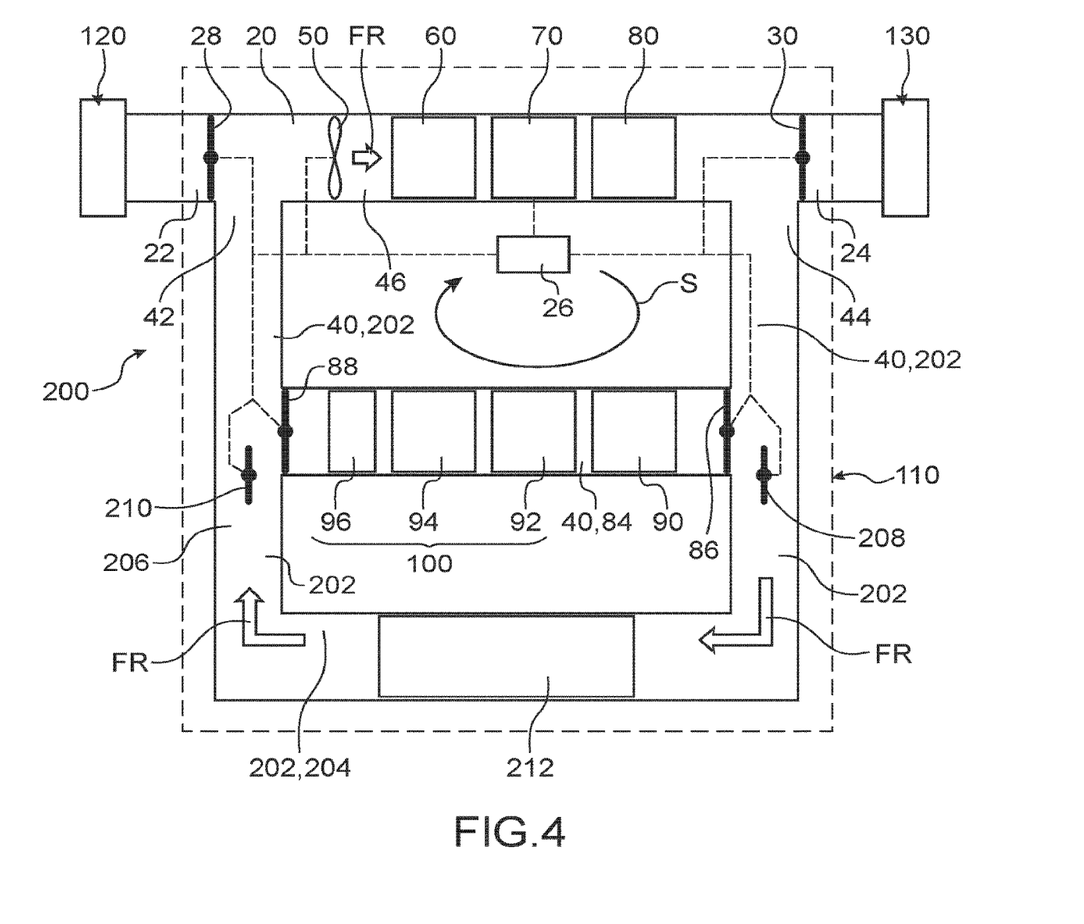

The gas treatment system 200 illustrated in FIGS. 3 and 4 comprises a second secondary path 202 not comprising the first active portion 84 and having two opposite ends connected to the main path 20, respectively upstream and downstream of the treatment portion 46. in the illustrated example, the two ends of the second secondary path 202 merge respectively with the two ends 42, 44 of the first secondary path 40.

Between these two opposite ends, the second secondary path 202 comprises a second active portion 204 not included in the first secondary path 40, and configured to modify the composition of the recirculation gas stream FR, in the regeneration mode.

The second secondary path 202 and at least the treatment portion 46 of the main path 20 form a second recirculation loop 206 (FIG. 4) enabling a closed-loop circulation of the recirculation gas stream FR in the treatment portion 46 of the main path 20, in the regeneration mode.

The switching device 26 is configured to cause a first recirculation phase and a second recirculation phase to follow one another, in which the recirculation gas stream FR circulates respectively in the first recirculation loop 48 (FIG. 3) and in the second recirculation loop 206 (FIG. 4), in the regeneration mode.

More precisely, the anti-bypass device is such that in its closed configuration, the anti-bypass device also obstructs (in a sealed manner) the second secondary path 202. The anti-bypass device thus prevents the main gas stream FT from bypassing the treatment portion 46 by passing via the second secondary path 202, in the treatment mode.

In its open configuration, the anti-bypass device alternately allows a circulation of the recirculation gas stream FR via the first secondary path 40 and the second secondary path 202.

To this effect, the first and second isolation valves 86 and 88 are arranged within the first secondary path 40, outside the second secondary path 202 (or at the limit thereof). Moreover, the anti-bypass device further comprises a third isolation valve 208 arranged upstream of the second active portion 204 in the second secondary path 202, outside the first secondary path 40 (or at the limit thereof), and a fourth isolation valve 210 arranged downstream of the second active portion 204 in the second secondary path 202, also outside the first secondary path 40 (or at the limit thereof).

The third and fourth isolation valves 208 and 210 are controlled by the control unit 26 such that:

the third and fourth isolation valves 208 and 210 isolate (in a sealed manner) the second active portion 204 of the second secondary path 202 of the main path 20, in the treatment mode, and isolate (in a sealed manner) the second active portion 204 of the second secondary path 202 of the first recirculation loop 48, in the first recirculation phase (FIG. 3), and such that the third and fourth isolation valves 208 and 210 place the second active portion 204 of the second secondary path 202 in communication with the main path 20 in the second recirculation phase (FIG. 4).

This configuration of the anti-bypass device can prevent the second active portion 204 acting on the main gas stream FT in the treatment mode and prevent the second active portion 204 acting on the recirculation gas stream FR in the first recirculation phase.

Moreover, the first and second isolation valves 86 and 88 are controlled by the control unit 26 such that the first and second isolation valves 86 and 88 isolate (in a sealed manner) the first active portion 84 of the first secondary path 40 of the second recirculation loop 206, in the second recirculation phase (FIG. 4).

The anti-bypass device can thus prevent the first active portion 84 acting on the recirculation gas stream FR in the second recirculation phase.

In the illustrated embodiment, the second active portion 204 comprises a particle filter 212.

Indeed, during the operation of the system in regeneration mode, the formation of organic aerosols can occur due to the chemical degradation of certain organic compounds. For example, in the case of the treatment of volatile organic compounds, reactions by nitrogen oxides (NOx) or by ozone (O3) can lead to the formation of semi-volatile species, in other words species with low vapour pressures. These products can be deposited at the surface of pre-existing particles (according to a heterogeneous condensation phenomenon) or can form new particles (according to a homogeneous nucleation phenomenon or gas-to-particle conversion).

The particle filter 212 makes it possible to capture such particles and thus avoid the contamination of the external environment by these particles.

Such a filter can be formed of a fibrous or electrostatic material.

The system 200 thus operates in an analogous manner to the operation of the system 10 of FIGS. 1 and 2, except for the regeneration mode. In the case of the system 200, this regeneration mode comprises successively:

the first recirculation phase, in which the first and second isolation valves 86 and 88 are open while the third and fourth isolation valves 208 and 210 are closed, whereby the recirculation gas stream FR circulates in the first recirculation loop 48 (FIG. 3), and has its composition modified in the manner described above with reference to the system 10; and the second recirculation phase, in which the first and second isolation valves 86 and 88 are closed while the third and fourth isolation valves 208 and 210 are open, whereby the recirculation gas stream FR circulates in the second recirculation loop 206 (FIG. 4), in which the particle filter 212 can capture any precipitated particles.

These two recirculation phases can optionally be implemented several times alternately, before a return to the treatment mode.

Figure 5:
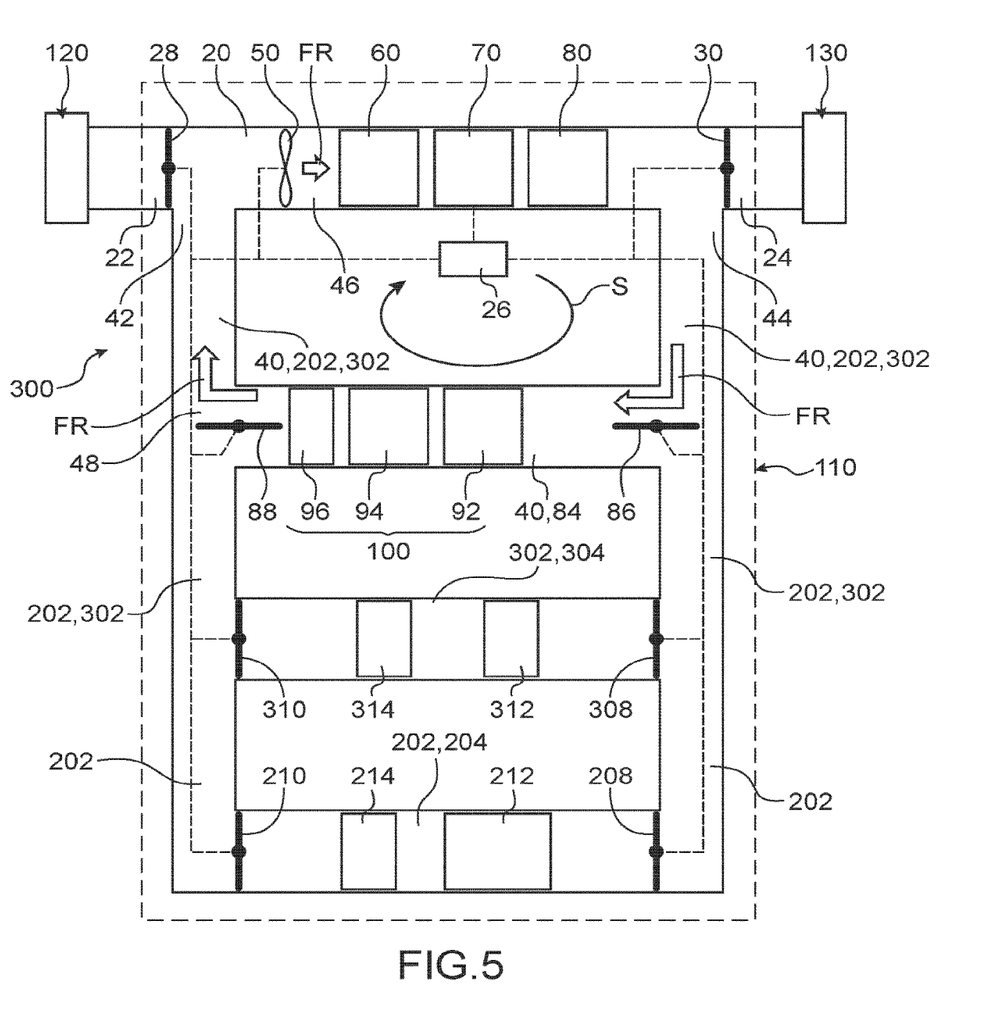
FIGS. 5 to 7 are views similar to FIG. 1, illustrating a gas treatment system according to a third preferred embodiment of the invention, operating respectively in three phases of its regeneration mode.
Figure 6:
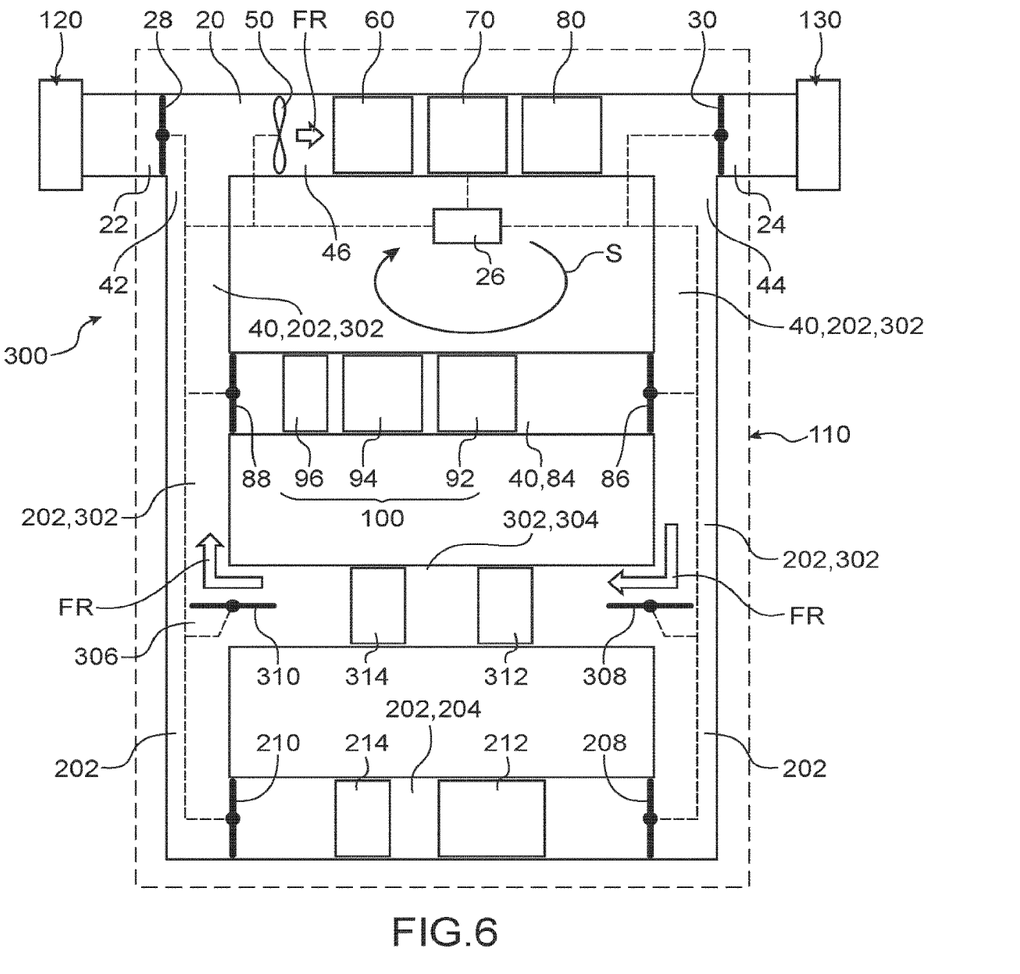
Figure 7:
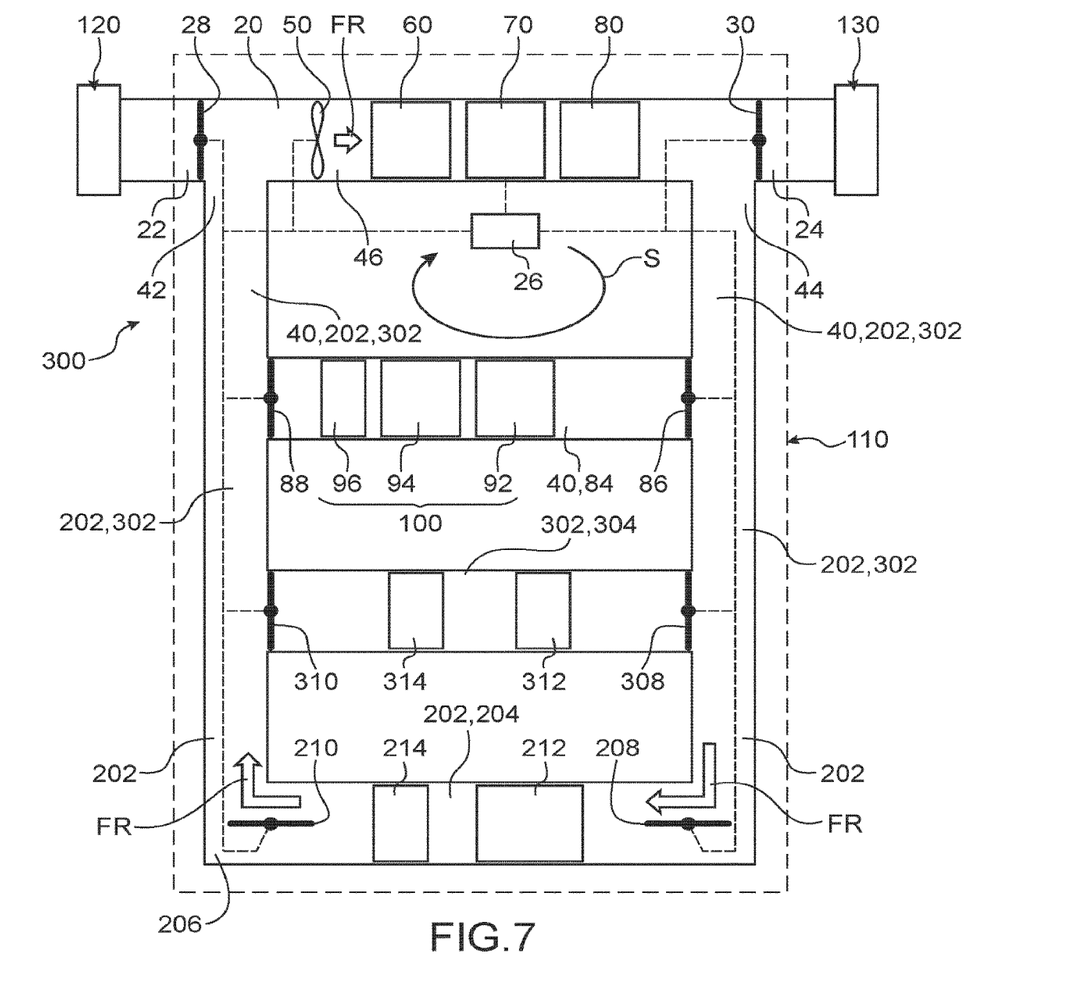

The gas treatment system 300 illustrated in FIGS. 5 to 7 is similar to the system 200 but differs from the latter in that the system 300 further comprises a third secondary path 302 not comprising the respective active portions 84, 204 of the first secondary path 40 and of the second secondary path 202, and having two opposite ends connected to the main path 20, respectively upstream and downstream of the treatment portion 46. In the illustrated example, the two ends of the third secondary path 302 merge respectively with the two ends 42, 44 of the first secondary path 40.

Between these two opposite ends, the third secondary path 302 comprises a third active portion 304 not included in the first secondary path 40 or in the second secondary path 202, and configured to modify the composition of the recirculation gas stream FR, in the regeneration mode.

The third secondary path 302 and at least the treatment portion 46 of the main path 20 form a third recirculation loop 306 (FIG. 6) enabling a closed-loop circulation of the recirculation gas stream FR in the treatment portion 46 of the main path 20, in the regeneration mode.

The switching device 26 is configured to cause a first recirculation phase, a second recirculation phase and a third recirculation phase to follow one another, in which the recirculation gas stream FR circulates respectively in the first recirculation loop 48 (FIG. 5), in the third recirculation loop 306 (FIG. 6) and in the second recirculation loop 206 (FIG. 7), in the regeneration mode.

More precisely, the anti-bypass device is such that in its closed configuration, the anti-bypass device also obstructs (in a sealed manner) the third secondary path 302. The anti-bypass device thus prevents the main gas stream FT from bypassing the treatment portion 46 by passing via the third secondary path 302, in the treatment mode.

In its open configuration, the anti-bypass device alternately allows a circulation of the recirculation gas stream FR via the first secondary path 40, the third secondary path 302 and the second secondary path 202.

To this effect, the first and second isolation valves 86 and 88 are arranged within the first secondary path 40, outside the second secondary path 202 (or at the limit thereof) and outside the third secondary path 302 (or at the limit thereof). Moreover, the third and fourth isolation valves 208 and 210 are arranged within the second secondary path 202, outside the first secondary path 40 (or at the limit thereof) and outside the third secondary path 302 (or at the limit thereof). The anti-bypass device further comprises a fifth isolation valve 308 arranged upstream of the third active portion 304 in the third secondary path 302, outside the first secondary path 40 (or at the limit thereof) and outside the second secondary path 202 (or at the limit thereof), and a sixth isolation valve 310 arranged downstream of the third active portion 304 in the third secondary path 302, likewise outside the first secondary path 40 (or at the limit thereof) and outside the second secondary path 202 (or at the limit thereof).

The fifth and sixth isolation valves 308 and 310 are controlled by the control unit 26 such that:

the fifth and sixth isolation valves 308 and 310 isolate (in a sealed manner) the third active portion 304 of the third secondary path 302 of the main path 20 in the treatment mode, isolate (in a sealed manner) the third active portion 304 of the third secondary path 302 of the first recirculation loop 48 in the first recirculation phase (FIG. 5), and isolate (in a sealed manner) the third active portion 304 of the third secondary path 302 of the second recirculation loop 206 in the third recirculation phase (FIG. 7), and such that the fifth and sixth isolation valves 308 and 310 place the third active portion 304 of the third secondary path 302 in communication with the main path 20 in the second recirculation phase (FIG. 6).

This configuration of the anti-bypass device can prevent the third active portion 304 acting on the main gas stream FT in the treatment mode and prevent the third active portion 304 acting on the recirculation gas stream FR in the first and the third recirculation phases.

Moreover, the first and second isolation valves 86 and 88 are controlled by the control unit 26 such that the first and second isolation valves 86 and 88 isolate (in a sealed manner) the first active portion 84 of the first secondary path 40 of the third recirculation loop 306, in the second recirculation phase (FIG. 6), and isolate the first active portion 84 of the first secondary path 40 of the second recirculation loop 206, in the third recirculation phase (FIG. 7).

The anti-bypass device can thus prevent the first active portion 84 acting on the recirculation gas stream FR in the second and third recirculation phases.

Finally, the third and fourth isolation valves 208 and 210 are controlled by the control unit 26 such that:

the third and fourth isolation valves 208 and 210 isolate (in a sealed manner) the second active portion 204 of the second secondary path 202 of the first recirculation loop 48, in the first recirculation phase (FIG. 5), and isolate (in a sealed manner) the second active portion 204 of the second secondary path 202 of the third recirculation loop 306, in the second recirculation phase (FIG. 6), and such that the third and fourth isolation valves 208 and 210 place the second active portion 204 of the second secondary path 202 in communication with the main path 20 in the third recirculation phase (FIG. 7).

This configuration of the anti-bypass device can prevent the second active portion 204 acting on the recirculation gas stream FR in the first recirculation phase and in the second recirculation phase.

In the illustrated embodiment, the second active portion 204 further comprises a trapping device 214 suitable for trapping at least one product of at least one reaction among the oxidation reactions of the predefined substances, and arranged downstream of the particle filter 212 with respect to the predetermined direction of circulation S.

Moreover, the third active portion 304 comprises a nitrogen oxides treatment device 312 similar to the nitrogen oxides treatment device 90 described above, in which case the first active portion 84 is devoid of this device 90.

In the illustrated example, the third active portion 304 further comprises a trapping device 314 suitable for trapping at least one product of at least one reaction among the oxidation reactions of the predefined substances, and arranged downstream of the nitrogen oxides treatment device 312 with respect to the predetermined direction of circulation S.

The system 300 thus operates in an analogous manner to the operation of the system 200 of FIGS. 3 and 4, except for the regeneration mode. In the case of the system 300, this regeneration mode comprises successively:

the first recirculation phase, in which the first and second isolation valves 86 and 88 are open, while the third, fourth, fifth and sixth isolation valves 208, 210, 308, 310 are closed, whereby the recirculation gas stream FR circulates in the first recirculation loop 48 (FIG. 5), and has its composition modified in the manner described above with reference to the system 10, except for the nitrogen oxides (NOx);

the second recirculation phase, in which the fifth and sixth isolation valves 308 and 310 are open, while the first, second, third and fourth isolation valves 86, 88, 208 and 210 are closed, whereby the recirculation gas stream FR circulates in the third recirculation loop 306 (FIG. 6), in which the nitrogen oxides treatment device 312 can reduce the concentration of nitrogen oxides in the recirculation gas stream FR;

the third recirculation phase, in which the third and fourth isolation valves 208 and 210 are open, while the first, second, fifth and sixth isolation valves 86, 88, 308 and 310 are closed, whereby the recirculation gas stream FR circulates in the second recirculation loop 206 (FIG. 7), in which the particle filter 212 can capture any precipitated particles.

In the illustrated example, the trapping devices 214 and 314 can capture any oxidation reaction products remaining in the recirculation gas stream FR, in the second and third recirculation phases.

The three recirculation phases can optionally be implemented several times alternately, before a return to the treatment mode.

Alternatively, the various secondary paths of the system may not comprise common portions and, in particular, may be connected to the main path 20 independently from one another.

The invention claimed is:

1. A gas treatment system capable of operating alternately in a treatment mode and in a regeneration mode, comprising:
an inlet and an outlet, and a main path connecting the inlet to the outlet and comprising a treatment portion so as to enable the circulation of a main gas stream from the inlet to the outlet, passing via the treatment portion, in the treatment mode;
at least one secondary path having two opposite ends connected to the main path, respectively upstream and downstream of the treatment portion, so that the secondary path and at least the treatment portion of the main path form a recirculation loop enabling closed-loop circulation of a recirculation gas stream in the treatment portion of the main path, in the regeneration mode;
a fan disposed in the recirculation loop and configured at least to propel the recirculation gas stream within the recirculation loop in a predetermined circulation direction, in the regeneration mode;
a first adsorption device disposed in the treatment portion of the main path, downstream of the fan with respect to the predetermined circulation direction, and capable of adsorbing predefined substances potentially present in the main gas stream, in the treatment mode;
an ozone generator disposed in the treatment portion of the main path, downstream of the fan with respect to the predetermined circulation direction, and capable of generating ozone in the regeneration mode; and
a switching device configured to keep the inlet and the outlet open, prevent the circulation of the main gas stream via the secondary path or each secondary path, and keep the ozone generator stopped, in the treatment mode, and to keep the inlet and the outlet closed, allow the circulation of the recirculation gas stream in the secondary path or in each secondary path, and keep the ozone generator in operation, in the regeneration mode;
wherein it further comprises a second adsorption device capable of adsorbing the predefined substances, disposed in the treatment portion of the main path, downstream of the fan with respect to the predetermined circulation direction, and such that the first and second adsorption devices are respectively disposed upstream and downstream of the ozone generator with respect to the predetermined direction of circulation.

2. The gas treatment system according to claim 1, wherein the secondary path comprises an active portion configured to modify the composition of the recirculation gas stream, in the regeneration mode.

3. The gas treatment system according to claim 2, wherein the active portion comprises a treatment assembly comprising a catalysis device suitable for catalysing at least one reaction among oxidation reactions of the predefined substances, and wherein the fan, the first adsorption device, the ozone generator, the second adsorption device and the treatment assembly are arranged in that order with respect to the predetermined direction of circulation.

4. The gas treatment system according to claim 3, wherein the treatment assembly further comprises an ozone treatment device suitable for trapping or breaking down ozone, and arranged downstream of the catalyst device with respect to the predetermined direction of circulation.

5. The gas treatment system according to claim 4, wherein the treatment assembly further comprises a trapping device suitable for trapping at least one product of at least one reaction among the oxidation reactions of the predefined substances, and arranged downstream of the ozone treatment device with respect to the predetermined direction of circulation.

6. The gas treatment system as claimed in claim 2, wherein the active portion comprises a nitrogen oxides treatment device, suitable for trapping nitrogen oxides.

7. The gas treatment system according to claim 3, wherein the active portion comprises a nitrogen oxides treatment device, suitable for trapping nitrogen oxides, and wherein the nitrogen oxides treatment device is arranged between the second adsorption device and the treatment assembly.

8. The gas treatment system according to claim 2, wherein the secondary path is a first secondary path, the active portion is a first active portion, and the recirculation loop is a first recirculation loop, the system further comprising a second secondary path not comprising the first active portion and having two opposite ends connected to the main path, respectively upstream and downstream of the treatment portion, so that the second secondary path and at least the treatment portion of the main path form a second recirculation loop allowing a closed-loop circulation of the recirculation gas stream in the treatment portion of the main path, in the regeneration mode, the second secondary path comprising a second active portion not included in the first secondary path and comprising at least one particle filter, the switching device being configured to cause a succession of recirculation phases in which the recirculation gas stream circulates respectively in the first recirculation loop and in the second recirculation loop, in the regeneration mode.

9. The gas treatment system according to claim further comprising a third secondary path not comprising the respective active portions of the first secondary path and of the second secondary path and having two opposite ends connected to the main path, respectively upstream and downstream of the treatment portion, so that the third secondary path and at least the treatment portion of the main path form a third recirculation loop allowing a closed-loop circulation of the recirculation gas stream in the treatment portion of the main path, in the regeneration mode, the third secondary path comprising a third active portion not included in the first secondary path or in the second secondary path and configured to modify the composition of the recirculation gas stream, in the regeneration mode, the switching device being configured to cause a succession of recirculation phases in which the recirculation gas stream circulates respectively in the first recirculation loop, in the third recirculation loop and in the second recirculation loop, in the regeneration mode.

10. The gas treatment system according to claim 9, wherein the third active portion comprises a nitrogen oxides treatment device, suitable for trapping nitrogen oxides.

11. The gas treatment system according to claim 1, wherein the fan is housed in the treatment portion of the main path and is configured to propel the main gas stream within the main path from the inlet to the outlet, in the treatment mode.

12. A method for gas treatment by means of the system according to claim 1, comprising, alternatively:
  using the system in the treatment mode, in which the switching device keeps the inlet and the outlet open, prevents the circulation of the main gas stream via the secondary path or each secondary path, and keeps the ozone generator stopped, whereby the main gas stream is admitted by the inlet, then passes into the first and second adsorption devices, wherein all or part of the predefined substances potentially present in the main gas stream are retained by adsorption, then the main gas stream, depleted of any predefined substances, is discharged via the outlet; and
  using the system in regeneration mode, in which the switching device keeps the inlet and the outlet closed, allows the circulation of the recirculation gas stream in the secondary path or in each secondary path, and keeps the ozone generator operating, whereby:
  a) the recirculation gas stream, driven by the fan in the recirculation loop, charges with ozone produced by the ozone generator and carries away the ozone and any active species induced by the ozone, into the second adsorption device, wherein any predefined substances previously adsorbed by the second adsorption device are oxidised and are desorbed on contact with the ozone and any other active species induced by the ozone,
  b) the first adsorption device receives the ozone, and any active species induced by the ozone, potentially backscattering into the recirculation gas stream, whereby any predefined substances previously adsorbed by the first adsorption device are oxidised and are desorbed on contact with the ozone and any active species induced by the ozone.

* * * * *